United States Patent
Mochizuki et al.

(10) Patent No.: US 7,264,626 B2
(45) Date of Patent: Sep. 4, 2007

(54) BLOOD VESSEL KNIFE

(75) Inventors: Yoshihiko Mochizuki, Mibu-machi (JP); Masaaki Matsutani, Takanezawa-machi (JP); Masatoshi Fukuda, Takanezawa-machi (JP); Maeko Sasanuma, Takanezawa-machi (JP)

(73) Assignee: MANI, Inc., Tochigi (JP)

( * ) Notice: Subject to any disclaimer, the term of this patent is extended or adjusted under 35 U.S.C. 154(b) by 606 days.

(21) Appl. No.: 10/694,327

(22) Filed: Oct. 27, 2003

(65) Prior Publication Data

US 2004/0153108 A1    Aug. 5, 2004

(51) Int. Cl.
*A61B 17/22*    (2006.01)
(52) U.S. Cl. ...................................... 606/159
(58) Field of Classification Search ............... 606/159, 606/167; 30/329–340
See application file for complete search history.

(56) References Cited

U.S. PATENT DOCUMENTS 3,893,238 A * 7/1975 Scholl .................... 30/294
5,342,379 A    8/1994 Volinsky
5,769,866 A * 6/1998 Frantzen .................. 606/167
6,113,616 A * 9/2000 Taylor et al. .............. 606/167
6,500,187 B1 * 12/2002 Petersen .................... 606/167

FOREIGN PATENT DOCUMENTS

DE            3225620 A1    2/1983

* cited by examiner

*Primary Examiner*—(Jackie) Tan-Uyen Ho
*Assistant Examiner*—Melanie Tyson
(74) *Attorney, Agent, or Firm*—Muramatsu & Associates

(57) ABSTRACT

A blood vessel knife allows a doctor to easily see a knife main body when holding it for surgical operation. In a blood vessel knife having a cutter holder at a tip portion of a rod-shaped grip, and a knife main body attached to a tip of the cutter holder, at least one of a first bent portion 2a formed at an end of the grip 2 and a second bent portion 3a formed on the cutter holder 3 is provided; the cutter holder 3 can be detachably engaged with the tip portion from either an inside or outside thereof; and an angle between the grip 2 and the knife main body is changeable whether the cutter holder is engaged from the inside or the outside of the tip portion. When gripping the blood vessel knife 1, doctors can easily see the knife main body 4 due to the second bent portion 3a, and the knife main body 4 diagonally penetrates a blood vessel 15 to prevent the knife main body 4 from penetrating a lower blood vessel wall 15b.

5 Claims, 8 Drawing Sheets

BLOOD VESSEL KNIFE

FIELD OF THE INVENTION

The present invention relates to a medical knife, and more particularly to a knife for incising coronary arteries.

RELATED ART

When constriction or occlusion (thrombus) occurs in coronary arteries of a heart, transplantation of a bypass blood vessel spanning the constricted or occluded portion is carried out. In this operation, a portion connecting blood vessels is incised with a blood vessel knife; a blade of scissors is inserted into the incision to enlarge it to a desired dimension; and an end of a blood vessel for transplantation is sutured to the enlarged portion to connect blood vessels with each other.

In case that the above transplantation of a bypass blood vessel is carried out, in recent years, the operation has been performed without stopping a heart, that is, while a heart has been running. This lightens burden of patients, and decreases operation cost. In this operation, it is the function of a blood vessel knife to make first incision to a blood vessel.

FIG. 7 is a front view of a conventional blood vessel knife. As illustrated in FIG. 7, the blood vessel knife 10 is composed of a grip 11, a cutter holder 12 and a knife main body 13. The grip 11 is formed to be a round rod made of stainless steel, and an approximately half portion 11a on a tip side is knurled to prevent a slippage. The cutter holder 12a is inserted in a tip of the grip 11 to connect the both with each other. This cutter holder 12 is, generally, made of synthetic resin. The knife main body 13 is inserted in a tip of the cutter holder 12 for mounting. The blood vessel knife 10 is formed to be linear overall length from the grip 11 to the knife main body 13.

FIG. 8A,8B show enlarged views of the cutter holder 12 in FIG. 7, in which FIG. 8A is a front view, and FIG. 8B is a bottom view. As shown in the views, the tip of the knife main body 13 is a sharp triangular portion, and a bottom side of the triangle of two sides containing the tip is in parallel to the axis of the grip 11, and the other side is a slope as a cutter 13a. The knife main body 13 is approximately 3 mm in length, which is rather short, so that it is not easy to find out the cutter 13a. Therefore, a projection 12a is formed on the cutter holder 12 to indicate that the cutter 13a is positioned on a side opposite to the projection 12a.

FIG. 9 shows a condition that the above blood vessel knife 10 incises a blood vessel 15. This blood vessel 15 is one of coronary arteries of a heart, and the blood vessel 15 is surrounded by body tissues such as a heart. The upper blood vessel wall 15a is on the surface side, and the area below the lower blood vessel wall 15b is a heart. In order to incise the blood vessel 15 as described above, in the past, the blood vessel knife 10 is slightly diagonally contacted to the blood vessel 15; the upper blood vessel wall 15a is penetrated by the tip of the knife main body 13; and the tip is moved by several millimeters so as not to penetrate the lower blood vessel wall 15b with the tip of the cutter to incise the blood vessel 15.

At this moment, the tip of the cutter must not penetrate the lower blood vessel wall 15b. When the tip of the knife main body 13 penetrates the upper blood vessel wall 15a, doctors feel a slight resistance as if they heard a sound "whoosh". Doctors take care that the slight resistance occurs only once, and become very nervous at this moment, since if the first resistance was not observed, there was a fear that the cutter might penetrate the lower blood vessel wall 15b.

Problems to be Solved by the Invention

However, since the conventional blood vessel knife is linear, as shown in FIG. 7, when a doctor tries to contact the knife main body 13 to the blood vessel 15 with his or her hand, it is difficult for him or her to see the knife main body 13 since it is covered by his or her hand. Further, since the knife main body 13 is slightly diagonally contacted to the blood vessel 15, it becomes difficult to see the tip of the cutter of the knife main body 13. When the blood vessel is not so thick and it moves by heartbeats (off pump state), the motion is more difficult. For the above reasons, the cutter is liable to penetrate the lower blood vessel wall 15b. In addition, it is preferable to change the angle that the knife main body 13 is contacted to the blood vessel 15 in accordance with the position of a patient or the preference of a doctor.

The present invention has been made to solve the above problems, and the object thereof is to provide a blood vessel knife, with which a doctor is easily able to see the knife main body 13 while holding it with his or her hand; it becomes easier to prevent the cutter from penetrating the lower blood vessel wall 15b during heartbeats; and the angle that the knife main body 13 is contacted to the blood vessel 15 is changeable in accordance with the positions of a patient or the preference of a doctor.

Means for Solving the Problems

In order to achieve the above object, a blood vessel knife of the first invention comprises: a rod-shaped grip; a cutter holder with a knife main body detachably attached to a tip portion of the grip; and a first bent portion formed at an end or both ends of the grip and/or a second bent portion formed to the cutter holder, wherein the cutter holder can be engaged with the tip portion of the grip either from inside or outside of the tip portion of the grip; and an angle between the grip and the knife main body is changeable depending on whether the cutter holder is engaged from the inside or the outside of the tip portion.

The above blood vessel knife may have the both first and second bent portions; the blood vessel knife may have the both first and second bent portions, and the first bent portions may be formed on both ends of the grip such that bent angles of the first portions at both ends of the grip are different from each other; the tip portion of the grip can be plate-like, and may be provided with a long hole at a central portion thereof and a slit at a tip thereof, and the cutter holder may have a first engagement portion engaging the long hole and a second engagement portion being inserted to the slit; the cutter holder can be provided with the second bent portion; on one side of the second bent portion may be a curved portion; at both ends of the curved portion can be the first and second engagement portions; and resiliency of the curved portion allows the first and second engagement portions to press-contact to the long hole and the slit respectively.

Further, in the above blood vessel knife, the angle between the grip and the knife main body can be between 10° and 60°; a cutter of the knife main body may face upward; and distance from the bent portion to the knife main body may be approximately 3 cm.

Operation of the Invention

When the grip of the blood vessel knife is gripped, the bent portion allows the knife main body to easily be seen over a hand gripping the grip. In addition, this bent portion causes the knife main body to penetrate nearly in parallel to a blood vessel as illustrated in FIG. 6. With the above construction, it becomes difficult that the knife main body penetrates the lower blood vessel wall.

With the construction that the cutter holder is detachable and a plurality of cutter holders with different bent angles are prepared, a cutter holder with a suitable bent angle can be selectable in accordance with conditions that the blood vessel knife is used. It is possible to change the bent angle by mounting the cutter holder from upside or downside of the tip portion.

BRIEF DESCRIPTION OF THE DRAWINGS

FIGS. 2A and 2B are enlarged views of a tip portion of a grip, in which FIG. 2A is a plan view, and FIG. 2B is a front view;

FIGS. 3A-3D are enlarged views of a cutter holder, in which FIG. 3A is a front view; FIG. 3B is a cross-sectional front taken along the line A-A of FIG. 3A; FIG. 3C is a view observed from B in FIG. 3A; and FIG. 3D is a cross-sectional view taken along the line C-C of FIG. 3A;

FIGS. 8A and 8B are enlarged views of a cutter holder shown in FIG. 7, in which FIG. 8A is a front view, and FIG. 8B is a bottom view.

DESCRIPTION OF THE PREFERRED EMBODIMENTS

Figure 1:
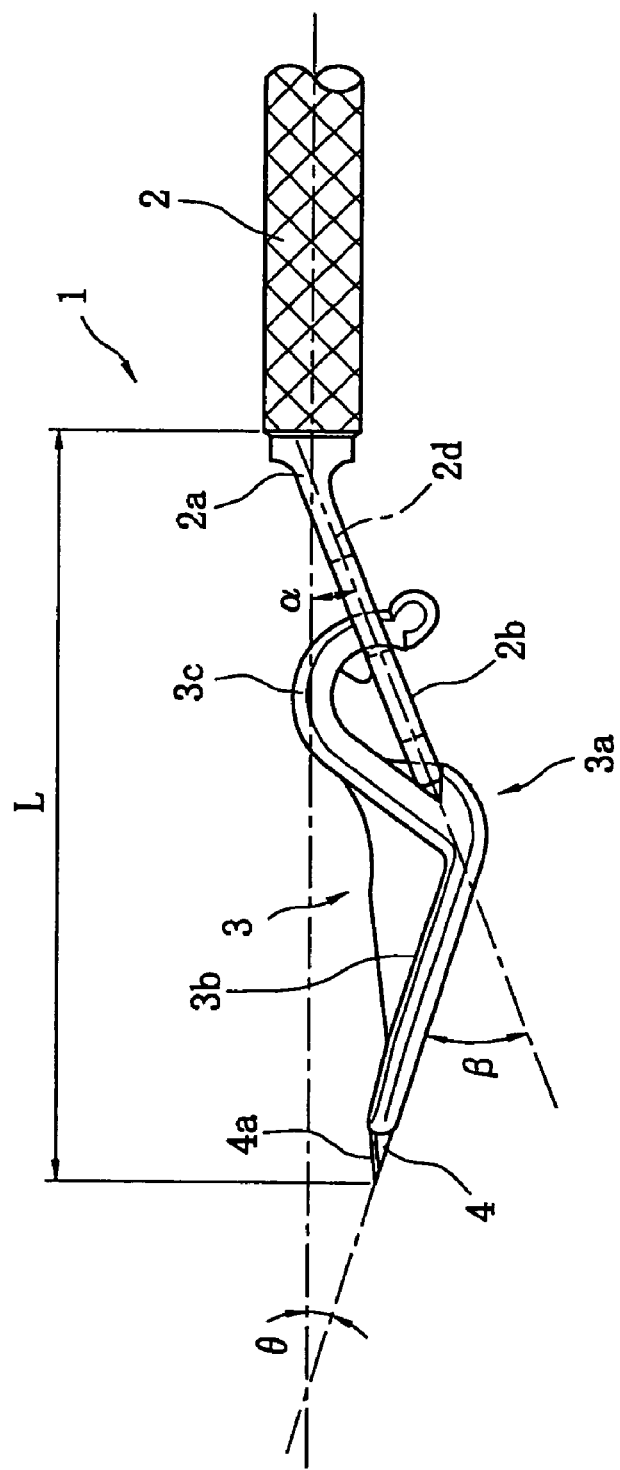
FIG. 1 is a front view showing a primary portion of a blood vessel knife according to an embodiment of the present invention.

Next, embodiments of the present invention will be explained with reference to drawings.

FIGS. 1 to 6 show an embodiment of the present invention. In a blood vessel knife 1 in this embodiment, a tip portion 2b of a grip 2 is bent at a first bent portion 2a, and to the tip portion 2b is detachably mounted a cutter holder 3 with a second bent portion 3a. The cutter holder 3 is integrally formed of synthetic resin, and at the tip of a haft portion 3b of the cutter holder 3 is attached a knife main body 4 of which cutter (cutting edge) 4a faces upward with respect to a blood vessel.

Figures 2A, 2B:
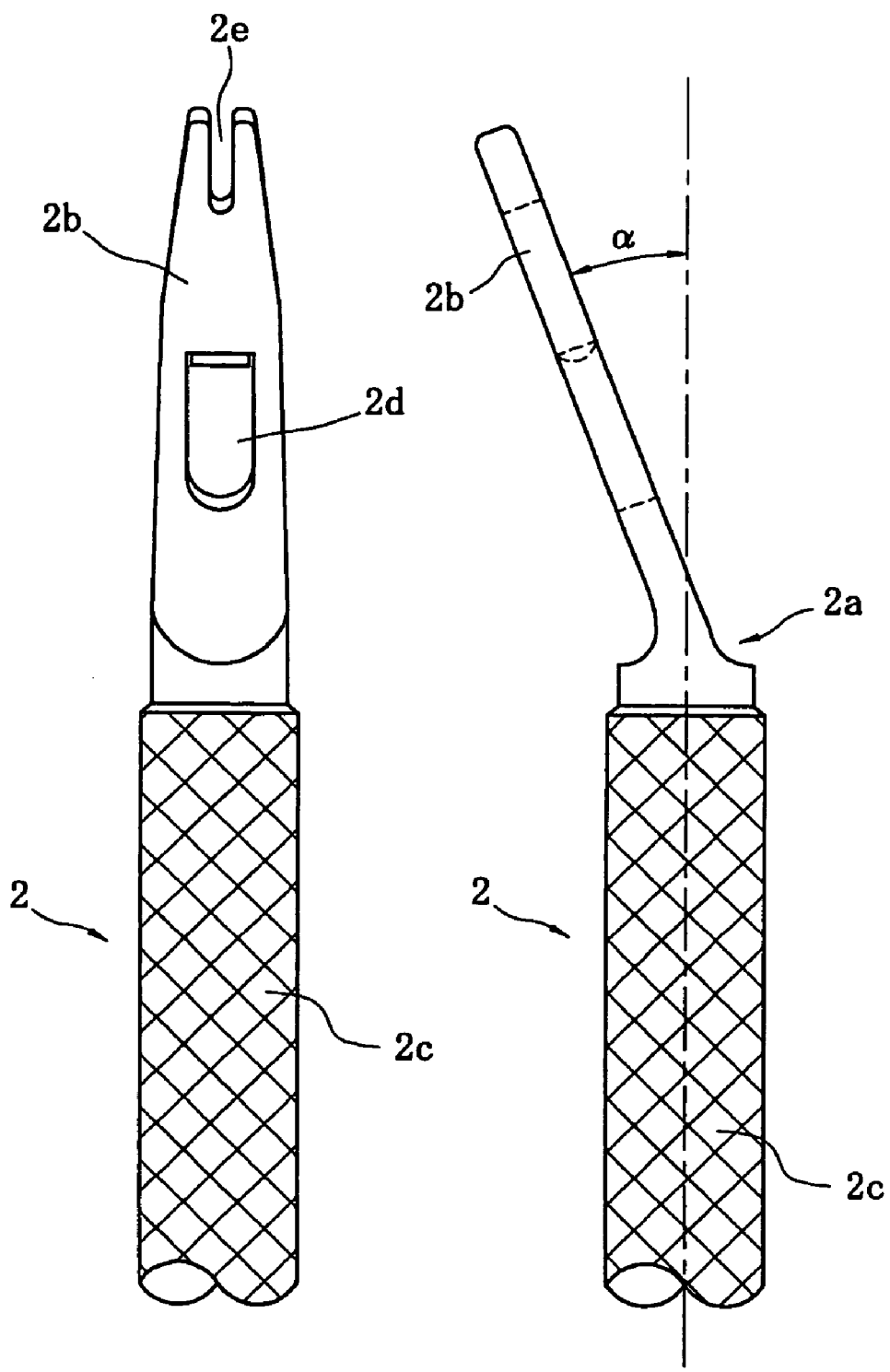

FIGS. 2A and 2B show enlarged views of the tip portion of the grip, in which FIG. 2A is a plan view, and FIG. 2B is a front view. The grip 2 to has a grip main body 2c and a tip portion 2b at the first bent portion 2a. The grip main body 2c is a solid or hollow cylinder made of stainless steel, and the outer surface thereof is knurled to prevent slippage. The tip portion 2b has a plate-like shape, and its shape is changed from a round to a plate at the first bent portion 2a, and the tip portion 2b is bent so as to make an angle α with the grip main body 2c. The tip portion 2b is provided with a substantially rectangular long hole 2d at the central portion thereof, and the tip portion 2b becomes gradually thinner from a position near the front edge of the long hole 2d toward the tip, and a slit 2e is formed in an axial direction thereof from the tip thereof.

Figure 3A:
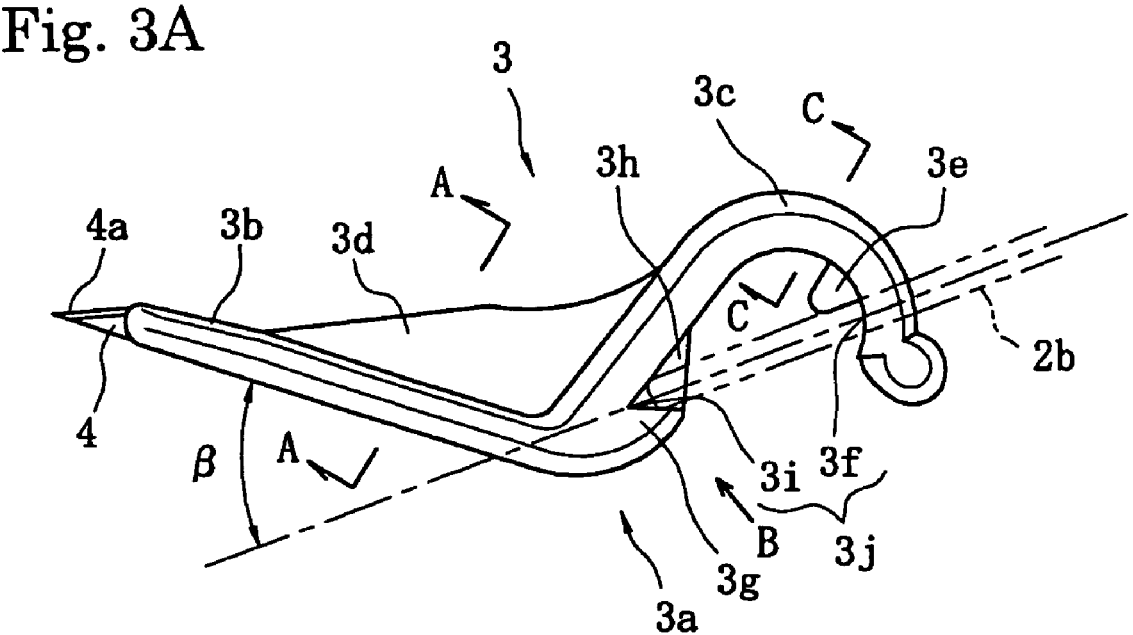
Figure 3B:
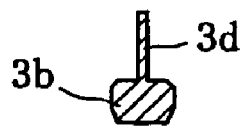
Figure 3C:
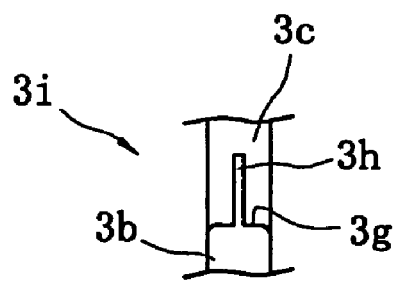
Figure 3D:

FIGS. 3A-3D are enlarged views of the cutter holder 3, in which FIG. 3A is a front view; FIG. 3D is a cross-sectional view taken along the line A-A of FIG. 3A; FIG. 3C is a view observed from B in FIG. 3A; and FIG. 3D is a cross-sectional view taken along the line C-C of FIG. 3A. The cutter holder 3 illustrated in the views is provided with the second bent portion 3a near the central portion thereof, and on one side of the second bent portion 3a is a bent portion 3c, which is made by bending a square pillar to form a character J, and on the other side is the haft portion 3b. As illustrated in FIG. 3C, the bent portion 3c and the haft portion 3b have the same width. The bent portion 3c has the dimension that enables its tip portion to enter the long hole 2d drilled on the tip portion 2b of the grip 2. The bent portion 3c and the haft portion 3b are reinforced by a plate-shaped reinforcing piece 3d. The tip of the bent portion 3c is enlarged and rounded, and at a portion slightly entering to a curved portion from an end is formed a projection 3e. Then, at the curved portion on the tip side from the projection 3e is formed a concaved portion 3f as a first engagement portion. On the haft portion 3b side of the bent portion 3c, a hook portion 3g projects toward the inside of the bent portion 3c, and a plate-shaped projection 3h stands in the same plane as the reinforcing piece 3d at the central portion of the hook portion 3g. The plate-shaped projection 3h has a thickness so that it can be inserted into the slit 2e that is formed at the tip of the grip 2. A concaved portion 3i as a second engagement portion is formed by the hook portion 3g and the plate-shaped projection 3h as shown in FIG. 3C. The concaved portion 3i is combined with the first engagement portion to constitute an engagement portion 3j for the tip portion 2b of the grip 2. As illustrated by phantom lines in FIG. 3A, when the tip portion 2b is engaged, the haft portion 3b bends so as to make an angle β with the tip portion 2b at the second bent portion 3a.

Figure 4:
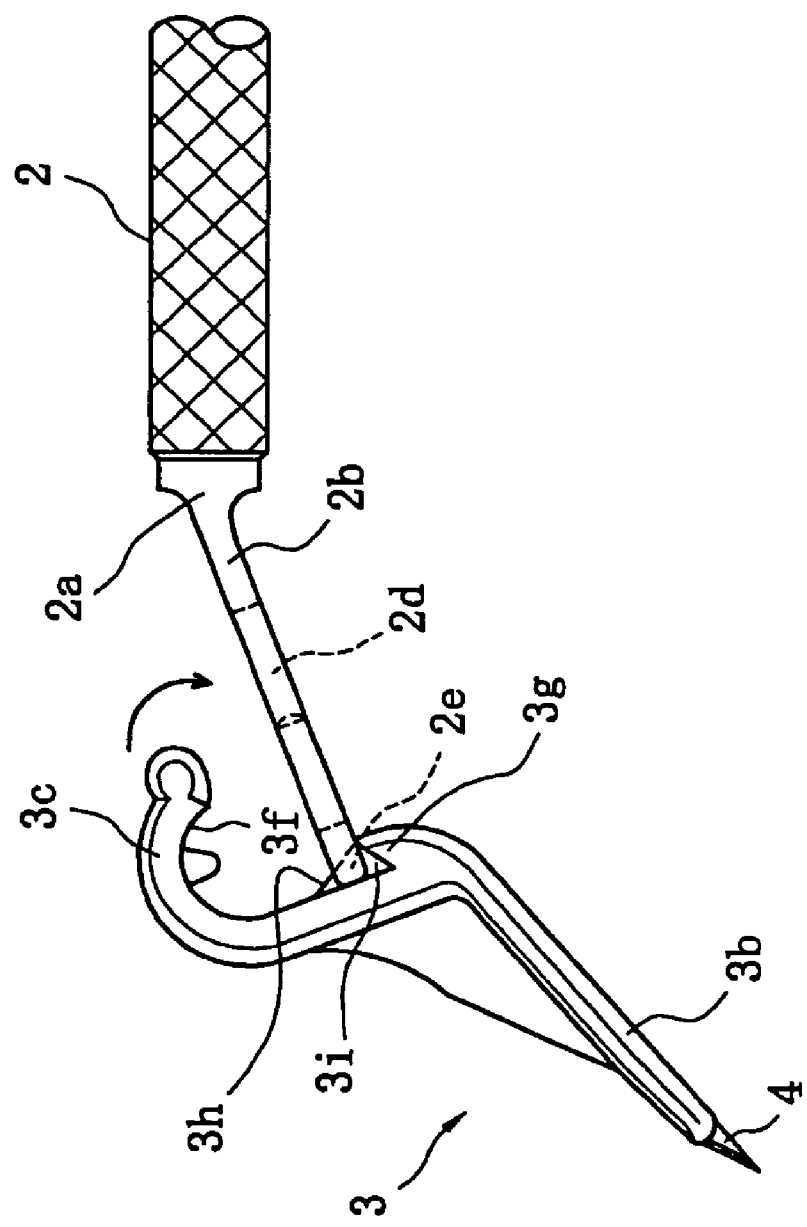
FIG. 4 is a view for explaining a manner to mount the cutter holder to the tip portion of the grip.

FIG. 4 is a view for explaining a manner to mount the cutter holder 3 to the tip portion 2b of the grip 2. In order to mount the cutter holder 3 to the tip portion 2b of the grip 2, at first, a side end portion of the hook portion 3g of the plate-shaped projection 3h of the cutter holder 3 is fit in the slit 2e at the tip of the tip portion 2b. Then, the cutter holder 3 is rotated about the engagement portion in a direction indicated by the arrow. As a result, the tip of the bent portion 3c reaches an edge on the tip side of the long hole 2d and stops there once. Pushing the tip of the bent portion 3c to the long hole 2d allows the tip of the bent portion 3c to cross an end on the tip side of the long hole 2d, and to penetrate the long hole 2d and project toward the opposite side, which causes the edge portion on the tip side of the long hole 2d to slip in the concaved portion 3f of the cutter holder 3. Since the cutter holder 3 is integrally formed of synthetic resin, the bent portion 3c is resilient, and the tip portion 2b is pressed against the concaved portion 3i at the opposite side, which allows the cutter holder 3 to securely be fixed to the tip portion 2b of the grip 2 as illustrated in FIG. 1. When removing the cutter holder 3, the cutter holder 3 is rotated in such a manner that the tip of the bent portion 3c is drawn out under the condition shown in FIG. 1 to realize the condition shown in FIG. 4 to dismount the cutter holder 3.

In this connection, the knife main body 4 may be mounted to the cutter holder 3 in advance, or it can be mounted after the cutter holder 3 is attached to the tip portion 2b of the grip 2.

In FIG. 1, the angle θ between the knife main body 4 and the grip 2 is formulated as θ=β−α, since the directions that the first bent portion 2a and the second bent portion 3a bend are opposite to each other.

Figure 5:
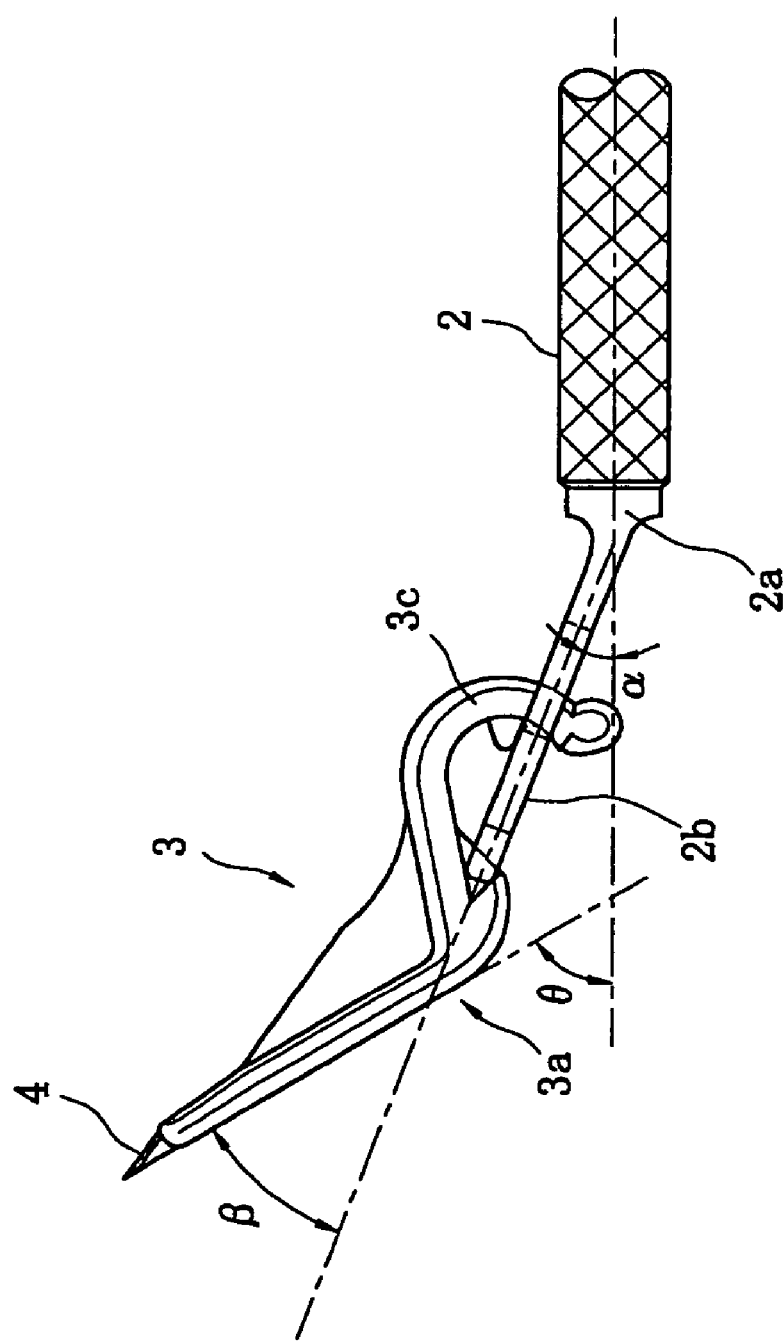
FIG. 5 is a front view showing a primary portion when the cutter holder is mounted to the tip portion of the grip from a side opposite to that shown in FIG. 1.

FIG. 5 is a front view showing a primary portion when the cutter holder 3 is mounted to the tip portion 2b of the grip 2 from a side opposite to that shown in FIG. 1. In the embodiment of the present invention, as illustrated in FIG. 5, the cutter holder 3 can be engaged from either sides, that is, from either inside or outside of the tip portion 2b. The manner to mount and dismount the grip 2 is the same as that of the embodiment shown in FIGS. 1 and 4.

In the engaged state shown in FIG. 5, the angle θ between the knife main body 4 and grip 2 is formulated as θ=β+α, since the directions that the first bent portion 2a and the second bent portion 3a bend in the same direction. Therefore, in this embodiment of the present invention, with one cutter holder 3, the angle between the knife main body 4 and the grip 2 are changeable in two ways.

In the above embodiment, the first bent portion 2a and the second bent portion 3a are formed, but it is also possible to form the second bent portion 3a only without bending the first bent portion 2a, that is, with the angle α at the first bent portion 2a set to be 0°. In such a case, plurality of cutter holders 3 with different bent angles can provide one blood vessel knife 1 with desired angles by changing the cutter holder 3 that mounted to the blood vessel knife 1. It is a matter of course that, on the contrary, only the first bent portion 2a is formed without bending the second bent portion 3a, that is, with the angle α at the second bent portion 3a set to be 0°.

Further, in the above embodiment, the tip portion 2b is formed on one end of the grip 2 only, but both ends of the grip 2 may have the tip portion 2b. In such a case, the bent angles at the first bent portions 2a are preferably designed in such a manner that one of the angles α is α1 and the other is α2. With this construction, θ is changeable in four ways as described below when the angle β at the second bent portion 3a of the cutter holder 3 is fixed:

θ1=α1−β;
θ2=α1+β;
θ3=α2−β; and
θ4=α2+β.

As a result, the most suitable angle is selectable in accordance with the conditions at operations.

In addition, when two kinds of cutter holder 3 are prepared, and two kinds of bent angles β1 and β2 at the second bent portion 3a are set, the angle θ, which is the angle between the grip and the knife main body 4, is changeable in eight ways as described below:

θ1=α1−β1;
θ2=α1+β1;
θ3=α1−β2;
θ4=α1+β2;
θ5=α2−β1;
θ6=α2+β1:
θ7=α2−β2; and
θ8=α2+β2.

The angles θ1 to θ8 are preferably set between 10° and 60°. When the angles θ1 to θ8 are too small, the same problems as the conventional blood vessel knife 10 arise since the shape from the grip 2 to the knife main body 4 becomes almost linear, and when the angles θ1 to θ8 are too large, it becomes difficult to grip the grip 2.

Figure 6:
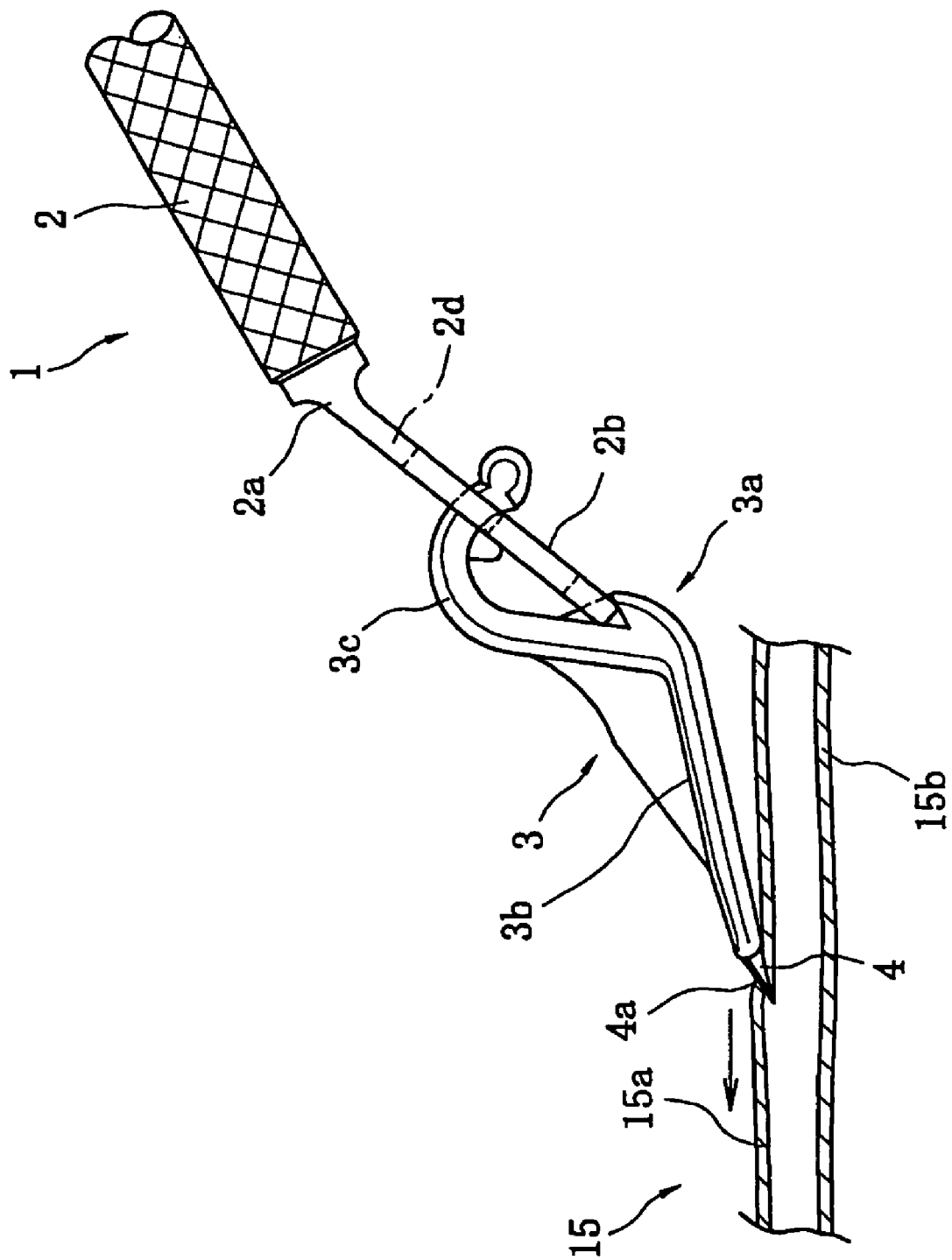
FIG. 6 is a view showing a condition that a blood vessel knife according to the present invention incises a blood vessel.
Figure 7:
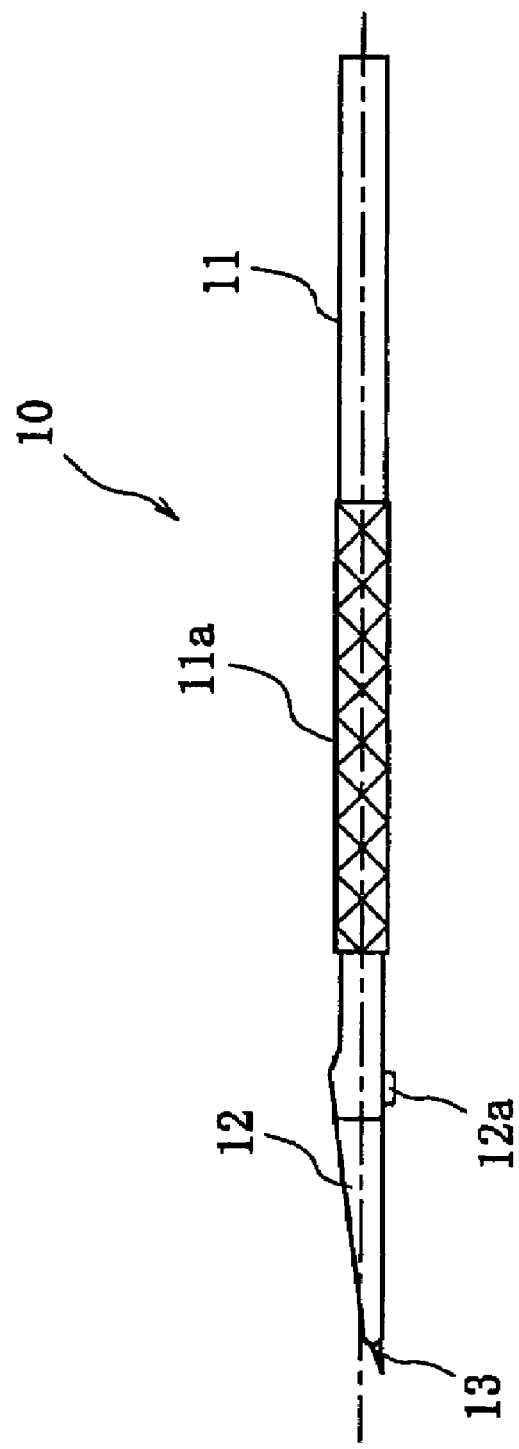
FIG. 7 is a front view of a conventional blood vessel knife.
Figure 8A:
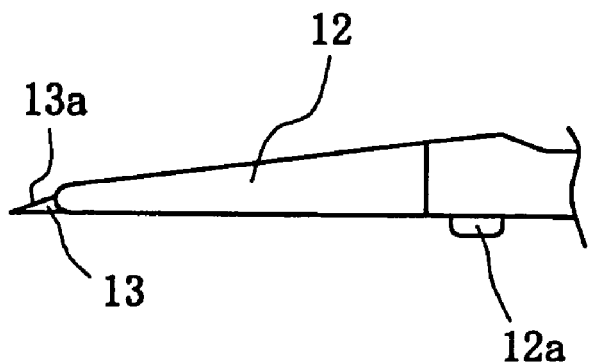
Figure 8B:
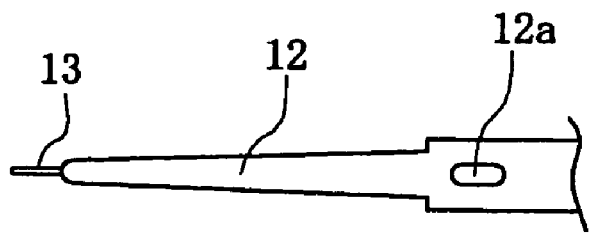
Figure 9:
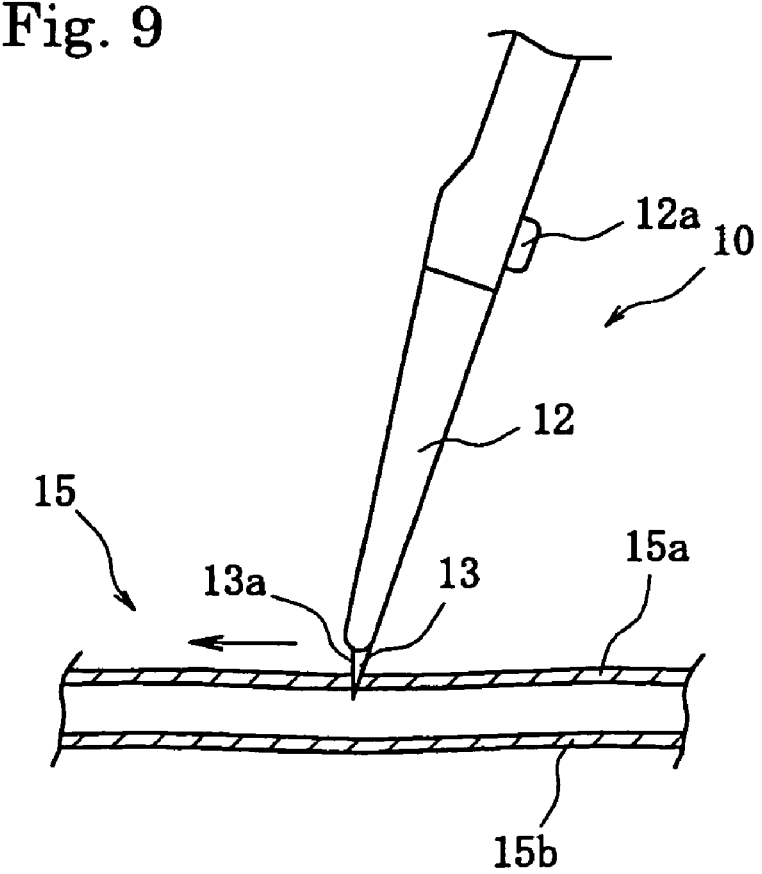
FIG. 9 is a view showing a condition that the blood vessel knife illustrated in FIG. 7 incises a blood vessel.

FIG. 6 shows a condition that the blood vessel knife 1 incises the blood vessel 15. The blood vessel knife 1 is diagonal against the grip 2 at the angles θ1 to θ8 as described above, so that the blood vessel knife 1 approaches to the blood vessel 15 almost in parallel to the blood vessel 15, and it penetrates the upper blood vessel wall 15a. At this moment, the bent portions 2a, 3a allow the grip 2 to bend at the angles between 10° and 60°, so that doctors can see the knife main body 4 clearly even though they grip the grip 2. As shown, the cutter (cutting edge) 4a mounted on the knife main body 4 is oriented upwardly with respect to the blood vessel 15. In addition, since the knife main body 4 diagonally contacts the blood vessel 15, there is a distance to the lower blood vessel wall 15b, and it takes longer time for the cutter 4a to reach the lower blood vessel wall 15b, which reduces the risk that the knife main body 4 penetrates the lower blood vessel wall 15b.

The moment the knife main body 4 of the blood vessel knife 1 penetrates the upper blood vessel wall 15a, the blood vessel knife 1 is moved in a direction indicated by the arrow in FIG. 6 by several millimeters to make the incision to a predetermined dimension. In this operation, since the knife main body 4 is inclined to the blood vessel 15, the distance to the lower blood vessel wall 15b can be kept long, which also reduces the risk to penetrate the lower blood vessel wall 15b. After that, the incision is enlarged with scissors for operation, and a bypass blood vessel is sutured so as to be connected to another blood vessel.

In the blood vessel knife 1 according to the second embodiment of the present invention, the distance L shown in FIG. 1 between the first bent portion 2a and the tip of the cutter 4a is preferably designed 2 to 5 cm. Below 2 cm, the tip of the knife main body 4 cannot be seen when doctors grip the blood vessel knife 1, and over 5 cm, it is difficult to use it since it becomes too long.

In this invention, it is also important that the cutter 4a is formed on the upper side of the knife main body 4. When penetrating the upper blood vessel wall 15a, the cutter 4a is positioned on the upper side of the knife main body 4, so that the cutter 4a enlarges the incision in such a manner to lift the blood vessel knife 1, which causes the cutter 4a to go away from the lower blood vessel wall 15b, resulting in less possibility of penetration of the lower blood vessel wall 15b.

In the above embodiment, the cross section of the grip 2 can be polygonal, which prevents the rotation of the blood vessel knife 1. Especially in the blood vessel knife 1 of the present invention, due to the first bent portion 2a, the blood vessel knife 1 is liable to rotate when put on a table, and there is a risk that the knife main body 4 stands still over the stand and cutter 4a touches a hand.

By the way, in the above embodiment, the grip 2 is knurled, but the present invention is not limited to the embodiment. Knurling is effective to prevent slipping, but there is another aspect that it is difficult to sterilize the knurled portion due to dirt entered thereto. Therefore, knurling is preferably applied to a cylindrical grip since it is relatively slippery, and a grip with polygonal cross section may not be knurled. As another embodiment, it is also possible not to knurl overall surface of the grip 2 but to knurl only half portion of the cutter holder 3 on the tip portion 2b side.

As described above, with this invention, in a blood vessel knife having a cutter holder at a tip of a rod-shaped grip, and a knife main body attached to a tip of the cutter holder, at least one of a first bent portion formed at an end or both ends of the grip and a second bent portion formed to the cutter holder that is detachably mounted to a tip portion of the grip is provided; the cutter holder can be engaged with the tip portion of the grip either from either inside or outside of the tip portion of the grip and projected from the opposite side; and an angle between the grip and the knife main body is changeable depending on whether the cutter holder is engaged from the inside or the outside of the tip portion, therefore, doctors can use the blood vessel knife while confirming the position of the knife main body over the hand gripping the grip in operations, which makes it easy to perform operations. In addition, with this invention, it becomes easy to prevent the knife main body from penetrating the lower blood vessel wall, which lightens stress of doctors and burden of patients. Further, one blood vessel knife can be used at two or more different angles, which makes it easier to cope with variety of conditions.

The invention claimed is:

1. A blood vessel knife, comprising:
a rod-shaped grip;
a cutter holder with a knife main body, the cutter holder being detachably attached to a tip portion of said rod-shaped grip;
a first bent portion formed on at least one end of the rod-shaped grip; and
a second bent portion formed on the cutter holder;
wherein said cutter holder engages with the tip portion of the rod-shaped grip from one side of either an inside or outside of the tip portion and projects from an opposite side of the tip portion; and an angle between the rod-shaped grip and the knife main body is changeable depending on whether the cutter holder is engaged with the tip portion from the inside or the outside of the tip portion; and
wherein a cutting edge of the knife main body is oriented upwardly with respect to a blood vessel to be cut.

2. A blood vessel knife, comprising:
a rod-shaped grip;
a cutter holder with a knife main body, the cutter holder being detachably attached to a tip portion of said rod-shaped grip; and
at least one of a first bent portion formed on one end of the rod-shaped grip and a second bent portion formed on the cutter holder, thereby creating a predetermined angle of the knife main body with respect to said rod-shaped grip;
wherein said tip portion of the rod-shaped grip has a plate-like shape, and is provided with a long hole that penetrates through one side to another side of the tip portion at a central portion thereof and a slit at a tip thereof; and said cutter holder has a first engagement portion that engages with said long hole and a second engagement portion that is inserted in the slit, thereby attaching the cutter holder to the tip portion of the rod-shaped grip; and
wherein said cutter holder engages with the tip portion of said rod-shaped grip either from an inside or outside of the tip portion of the grip thereby changing the angle between said rod-shaped grip and said knife main body depending on whether said cutter holder is engaged from the inside or the outside of the tip portion.

3. The blood vessel knife as claimed in claim 2, wherein said angle between the grip and the knife main body is between 10° and 60°.

4. The blood vessel knife as claimed in claim 2, wherein a cutter of said knife main body is formed linearly and oriented upwardly.

5. The blood vessel knife as claimed in claim 2, wherein a distance from said first bent portion to said knife main body is approximately 3 cm.

* * * * *